US006776789B2

(12) United States Patent
Bryant et al.

(10) Patent No.: US 6,776,789 B2
(45) Date of Patent: Aug. 17, 2004

(54) CINCH SUTURE AND METHOD FOR USING

(76) Inventors: Todd Bryant, 1119 Clyde Edgerton, Kernersville, NC (US) 27284; G. Leon Robbins, III, 744 Big Tree Dr., Lewisville, NC (US) 27023

( * ) Notice: Subject to any disclaimer, the term of this patent is extended or adjusted under 35 U.S.C. 154(b) by 213 days.

(21) Appl. No.: 09/835,153

(22) Filed: Apr. 16, 2001

(65) Prior Publication Data

US 2002/0151932 A1 Oct. 17, 2002

(51) Int. Cl.$^7$ .............................................. A61B 17/04
(52) U.S. Cl. ...................... 606/213; 606/151; 606/157; 606/228; 606/233
(58) Field of Search ................................ 606/151, 157, 606/213, 216–218, 228, 233; 24/16 PB, 17 AP, 30.5 P, 30.5 R (56) References Cited

U.S. PATENT DOCUMENTS

| 5,403,346 A | * | 4/1995 | Loeser ........................ 606/228 |
| 5,810,854 A | * | 9/1998 | Beach ......................... 606/151 |
| 6,196,033 B1 | * | 3/2001 | Dowdle ......................... 70/16 |
| 6,317,934 B1 | * | 11/2001 | Hiroki et al. ............. 24/16 PB |

* cited by examiner

Primary Examiner—John J. Calvert
Assistant Examiner—Robert H. Muromoto (57) ABSTRACT

This invention is a cinch suture having first and second segments and a locking device joining these segments which responds to teeth on the first segment to lock a ligature in place and prevent loosening. The locking device has teeth positioned to interact with engaging elements carried by the first segment as it is passed through the locking device to prevent removal. The locking device teeth are flexible and movable and arranged in two rows in a face to face offset relationship. The first segment engaging elements have a spherical configuration. The first segment passing through the locking device forms an endless loop for encircling and closing an opening formed by surgical excision of an organ or vessel. The locking mechanism has a receiving entrance and a removal exit. The two rows of offset teeth alternately engage spherical engaging elements to provide minute adjustment in the tightness of the suture and place pressure on the suture to hold it firmly in place. A method for producing the cinch suture is also described.

10 Claims, 11 Drawing Sheets

CINCH SUTURE AND METHOD FOR USING

BACKGROUND OF THE INVENTION

1. Field of the Invention

The present invention relates to a ligature and more particularly to a cinch suture for use during surgery primarily on small animals and a method for using the cinch suture.

2. Description of the Prior Art

Closing surgically an excised opening within a human or an animal organ or vessel can be a difficult procedure since closing the excised opening to prevent bleeding and induce healing must oftentimes be done in an area where the operable location cannot be seen. Many times it is done by feeling only.

Various techniques have been developed to tie sutures to hold an organ or vessel in a stable condition until bleeding subsides. See, for example, U.S. Pat. Nos. 5,601,577; 5,609,597; 5,643,289 and 5,911,728. Such techniques usually require the use of additional equipment or special machined parts to assist in the tying. This is expensive and is better replaced by a simple device that can be utilized by feel or limited view.

When devices of the type desired have been developed, it is oftentimes difficult to place the device in the correct location and apply the necessary motion to tighten it sufficiently to stop bleeding and induce healing. Many times, such a device cannot be sufficiently tightened to totally terminate bleeding.

In other cases where such devices have been developed for use, a standard size device has been provided which will function adequately if the organ or vessel is consistent with that size but which will not be completely efficient and effective in the event the organ or vessel size is smaller or larger than that contemplated by the standard size of the device.

In most cases, conventional methods of applying an effective way to terminate bleeding and induce healing is quite time consuming and tedious thus becoming very expensive. Moreover, the inability to see where the activity is taking place results in a lack of confidence in the surgical technique employed.

Because of the limitations experienced and noted in the prior art, there is perceived a definite need for an improved and simplified device for dealing with surgical excision in a reliable way to ensure stoppage of bleeding and the inducement of healing. It is to that perceived need that the present invention is directed.

OBJECTIVES AND BRIEF SUMMARY OF THE INVENTION

From the forgoing, it is apparent a primary objective of the present invention is to provide an improved ligature that includes all of advantages of prior art devices and none of the disadvantages.

Another objective of the present invention is to provide a faster, more reliable and more consistent surgical ligature material for use in surgical excisions.

A further objective of the present invention is to provide a locking mechanism for the new ligature which will not allow the ligature to loosen during any part of the placement or tightening process.

Yet another objective of the present invention is to provide the ability to furnish a ligature having a diameter, length and stretch of various sizes which will be consistent with the size needed.

A further objective of the present invention is to provide a device that will save time and money, that is reliable and consistent, and enhances confidence in the surgical technique employed.

From these objectives it can be seen that the present invention includes first a cinch suture having first and second segments and a locking mechanism joining these segments wherein the locking mechanism reacts to formations on the first segment to lock the ligature in place and prevent loosening thereafter. The locking mechanism has rows of teeth positioned to interact with engaging elements carried by the first segment as the first segment is passed through the locking mechanism to secure the first segment against removal. The locking mechanism teeth are flexible and movable and include preferably two rows of teeth that are in a face to face offset relationship. The first segment engaging elements have a spherical configuration, and the first segment passing through the locking mechanism forms an endless loop for encircling and closing an opening form by surgical excision of an organ or vessel.

The locking mechanism has a segment receiving entrance and a segment removal exit which facilitates the positioning of the first segment into the segment receiving entrance and out of the segment removal exit. The two rows of offset teeth alternately engage spherical engaging elements thereagainst to provide minute adjustment in the tightness of the suture and place pressure on the suture to hold it firmly in place.

The invention also includes a method of applying the cinch suture which includes passing the first segment through the locking mechanism to form an endless loop, positioning the endless loop around the opening, pulling the first segment through the locking mechanism to tighten the loop and close the opening while holding the second segment in a fixed position, and removing the unused portions of the first and second segments.

The inventive concept also contemplates a method for producing the cinch suture described herein which is to mold the cinch suture as an integral element and to vary the sizes of each molded unit to fit the need to which it will be used.

Thus there has been outlined the more important features of the invention in order that the detailed description that follows may be better understood and in order that the present contribution to the art may be better appreciated. There are, of course, additional features of the invention that will be described hereinafter and which will form the subject matter of the claims appended hereto. In that respect, before explaining at least one embodiment of the invention in detail, it is to be understood that the invention is not limited in its arrangement of the components set forth in the following description and illustrated in the drawings. The invention is capable of other embodiments and of being practiced and carried out in various ways.

It is also to be understood that the phraseology and terminology employed herein are for the purpose of description and should not be regarded as limiting in any respect. Those skilled in the art will appreciate that the concept upon which this disclosure is based may readily be utilized as a basis for designing other structures, methods and systems for carrying out the several purposes of this development. It is important that the claims be regarded as including such equivalent methods and products resulting therefrom that do not depart from the spirit and scope of the present invention. The application is neither intended to define the invention, which is measured by its claims, nor to limit its scope in any way.

Thus, the objects of the invention set forth above, along with the various features of novelty which characterize the invention, are noted with particularity in the claims annexed to and forming a part of this disclosure. For a better understanding of the invention, its operating advantages and the specific results obtained by its use, reference should be made to the following detailed specification taken in conjunction with the accompanying drawings wherein like characters of reference designate like parts throughout the several views.

The drawings are included to provide a further understanding of the invention and are incorporated in and constitute a part of this specification. They illustrate embodiments of the invention and, together with their description, further serve to explain the principles of the invention.

DETAILED DESCRIPTION OF PREFERRED EMBODIMENTS

Figure 1:
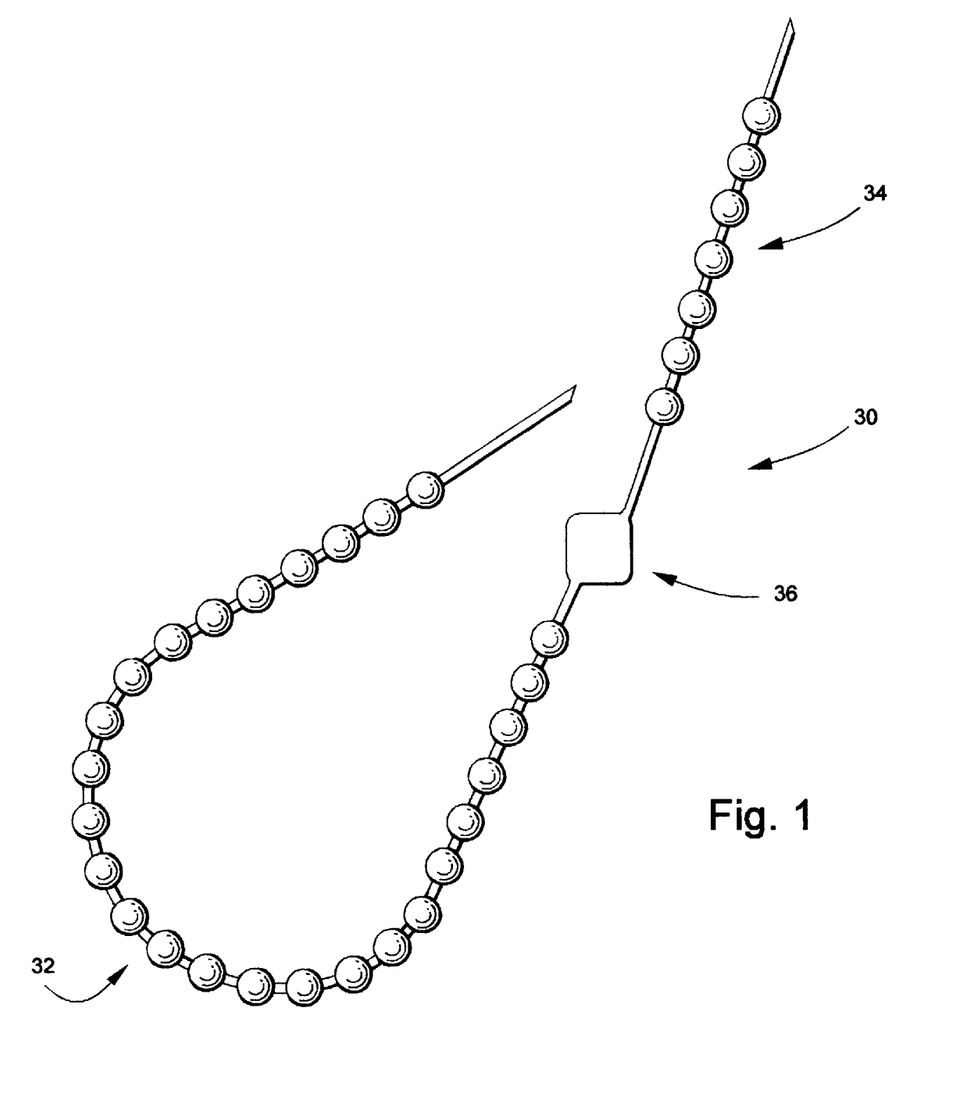
FIG. 1 is a plan view of the cinch suture comprising the present invention showing the first and second segments and the locking mechanism.
Figure 2:
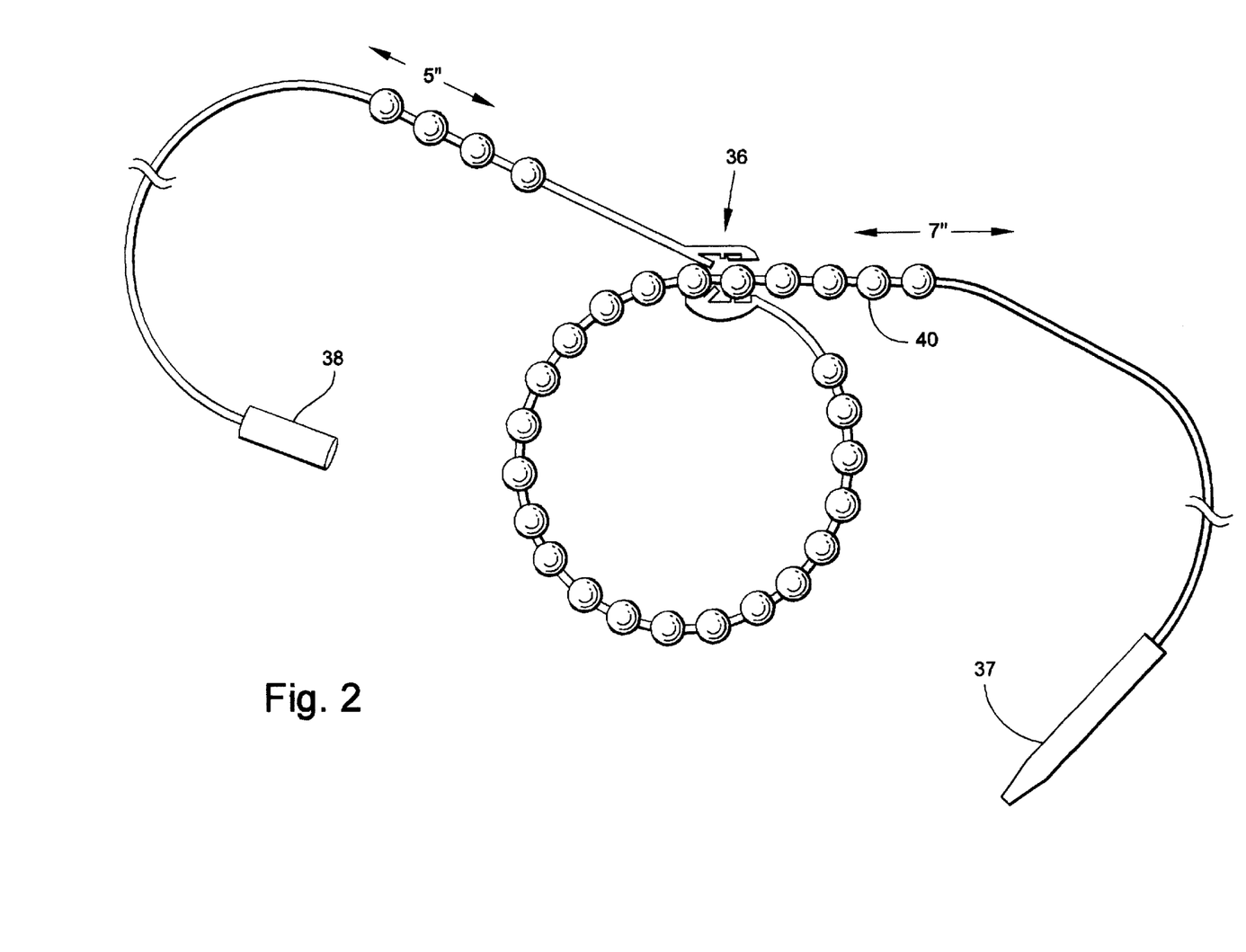
FIG. 2 is a plan view of the cinch suture shown in FIG. 1 wherein the first segment has been passed into and through the locking mechanism to form an endless loop.

Referring now to the drawings and particularly to FIG. 1, a ligature shown generally as 30, hereafter referred for convenience as a cinch suture, has a first segment 32, a second segment 34 and a locking mechanism 36. First segment 32 has a working end 38 and second segment 34 has a stationary end 37, these ends being joined through segments 32, 34 and locking mechanism 36. First segment 32 carries a plurality of engaging elements 40, and locking mechanism 36 has rows 42 of teeth 44 positioned to interact with some of engaging elements 40 as first segment 32 is passed through locking mechanism 36 to secure first segment 32 against removal.

Figure 3:
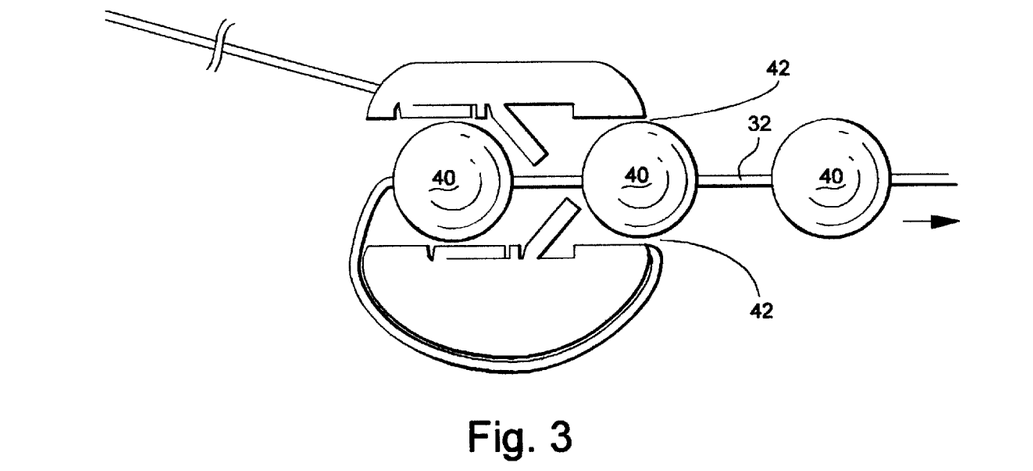
FIG. 3 is a side elevational, enlarged and diagrammatical view of the locking mechanism in the closed and loop securing position.
Figure 4:
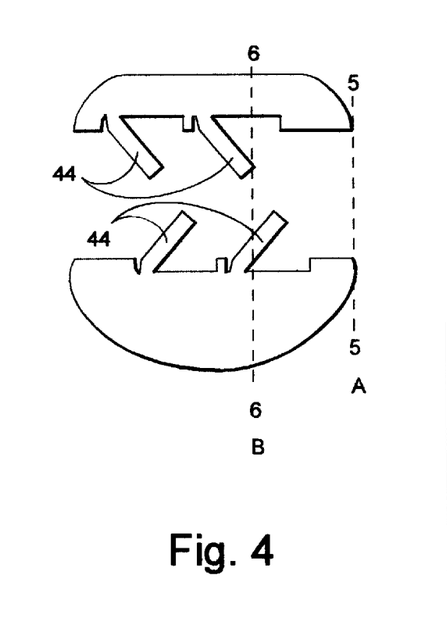
FIG. 4 is a side elevational and enlarged view of the locking mechanism shown in FIG. 3 in the open position.

Locking mechanism 36 is particularly described and illustrated in FIGS. 3 through 7 wherein offset teeth 44 on each of the two rows 42 face each other and interact with engaging elements 40 as they sequentially pass thereagainst. As can be seen in FIG. 3, engaging elements 40 are carried by segment 32 and depress in sequence legs 44 as they are moved through locking mechanism 36. Legs 44 carried by rows 42 are offset from each other in opposing rows so that they will permit minute adjustment in the tightness of the suture, and the other teeth will help to place pressure on the suture to hold it firmly in place. While a single row of teeth would be effective to secure engaging elements 40, the minute adjustment permitted when using two rows is preferred.

Figure 7:
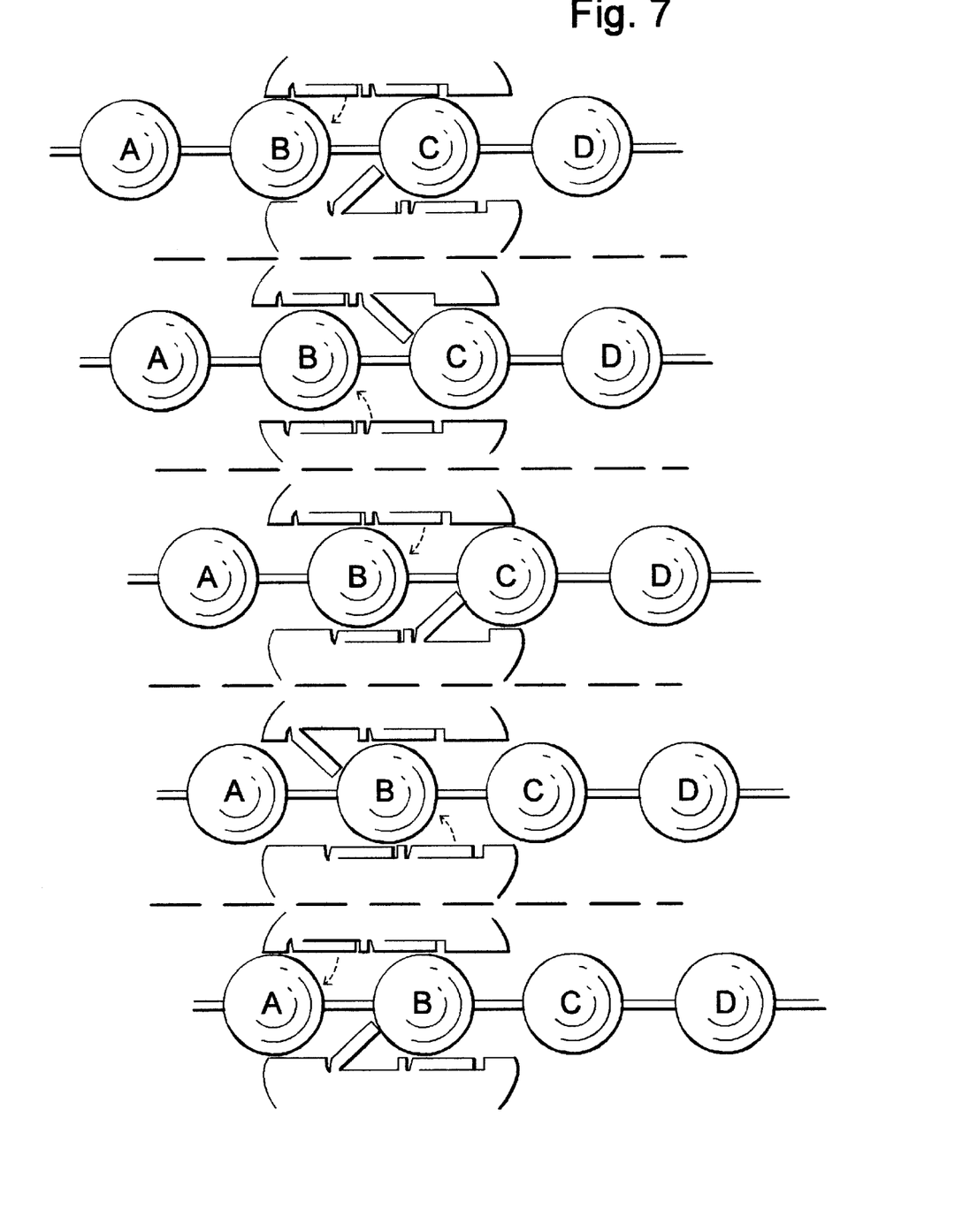
FIG. 7 is a series of diagrams showing the cooperation between the teeth of the locking mechanism and a plurality of engaging elements.
Figure 8:
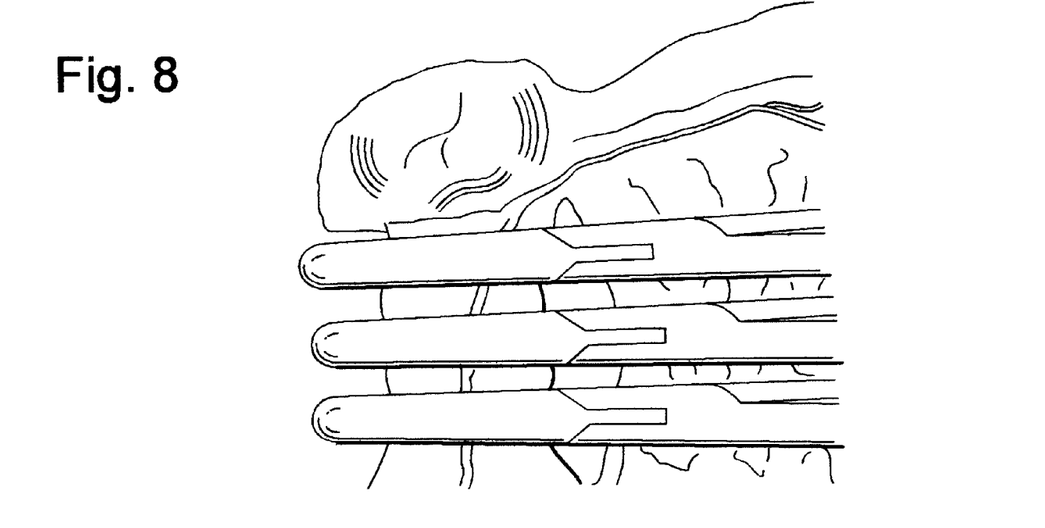
FIG. 8 is a plan, fragmentary and enlarged view of the beginning of a surgical excision wherein clamps have isolated an ovary of an animal from the ovarian pedicle.
Figure 9:
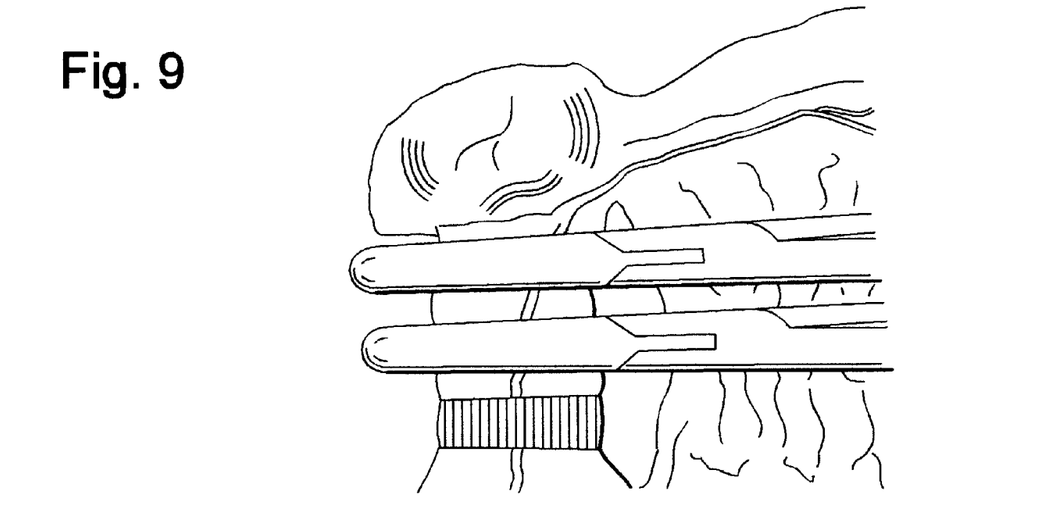
FIG. 9 is a plan view of the device shown in FIG. 8 wherein one of the clamps has been removed.
Figure 10:
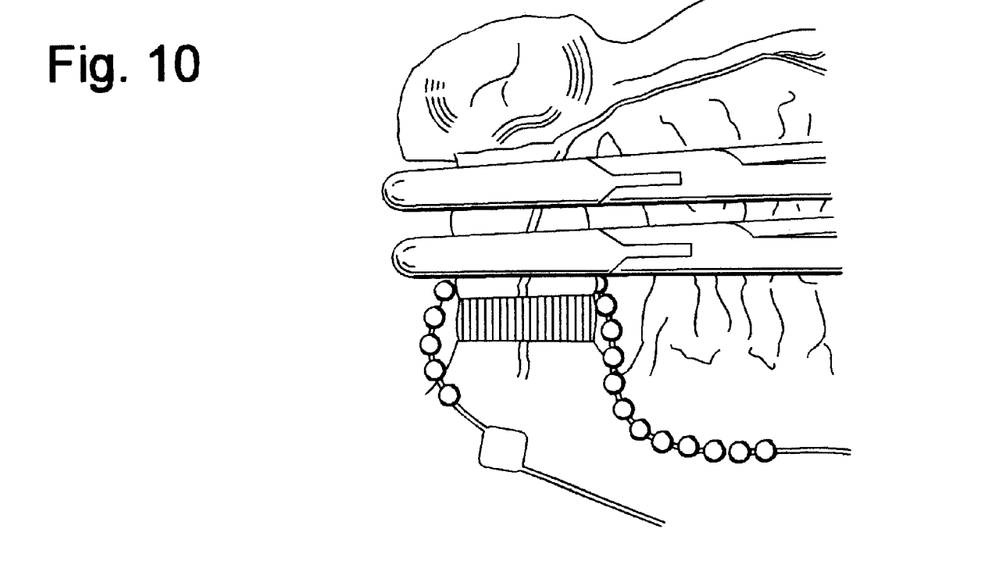
FIG. 10 is a plan view such as shown in FIG. 8 wherein the cinch suture has been placed around the ovarian pedicle.
Figure 11:
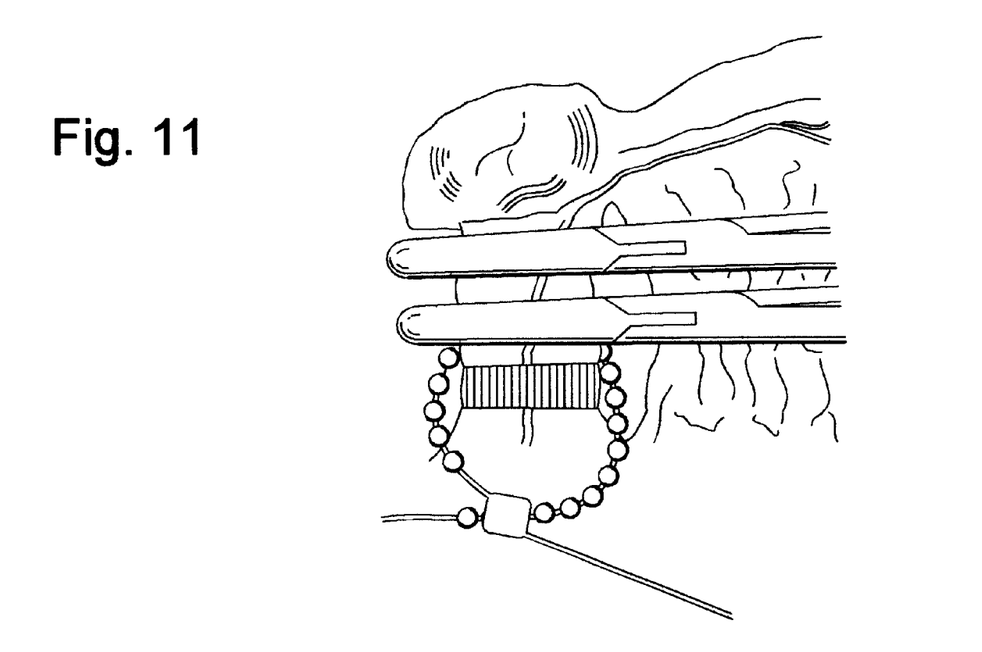
FIG. 11 is a plan view such as shown in FIG. 8 wherein the first segment has been inserted into the locking mechanism.
Figure 12:
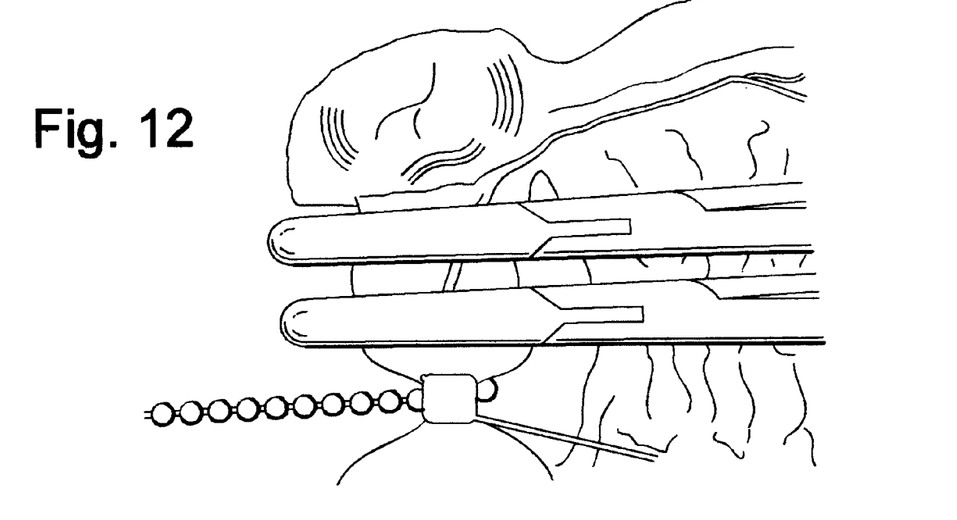
FIG. 12 is a plan view such as shown in FIG. 8 wherein the suture has been cinched down securely.
Figure 13:
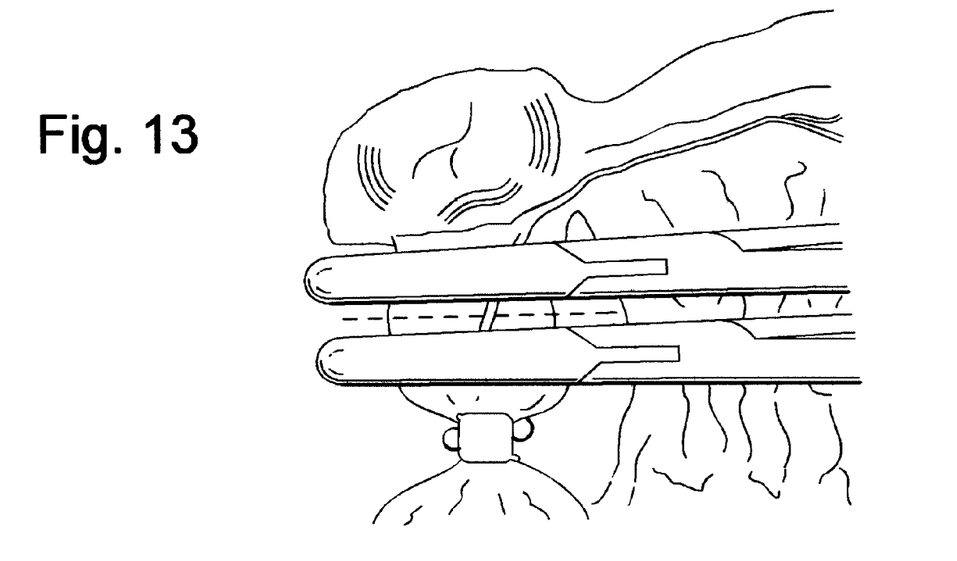
FIG. 13 is a plan view such as shown in FIG. 8 wherein the incision location has been identified.
Figure 14:
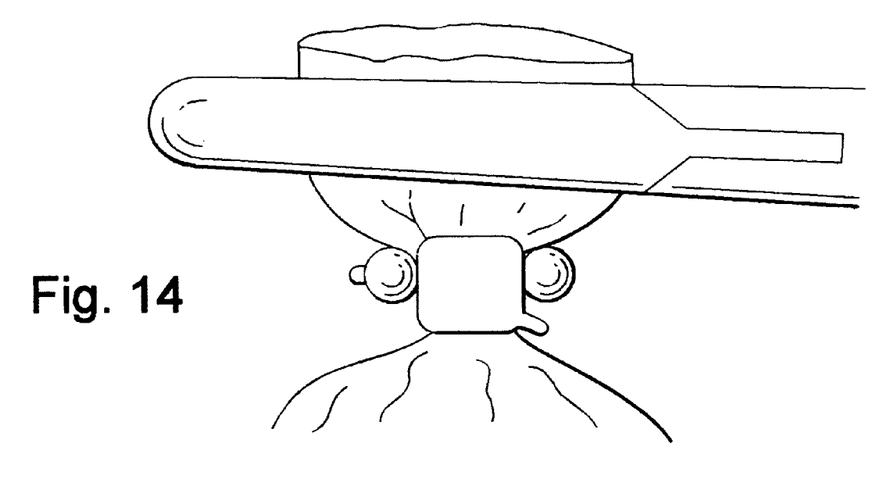
FIG. 14 is a plan view such as shown in FIG. 8 wherein one ovary has been removed and one clamp is still in place.
Figure 15:
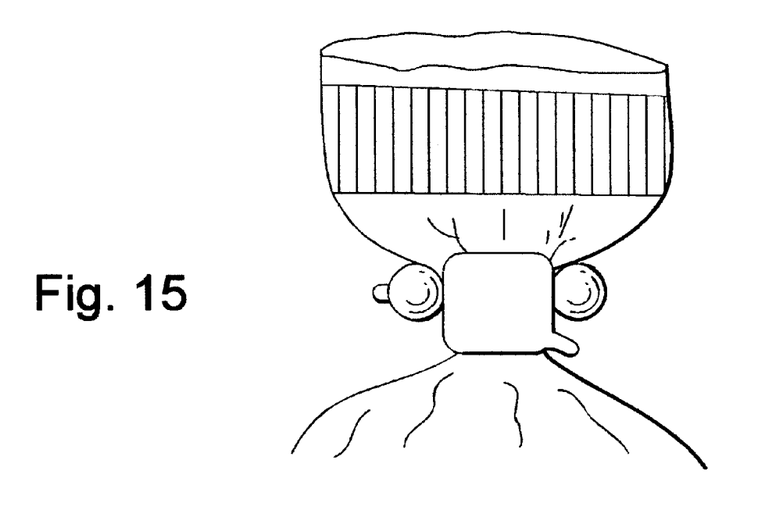
FIG. 15 is plan view such as shown in FIG. 8 wherein the ovary wherein the excision location is being inspected for hemorrhage.
Figure 16:
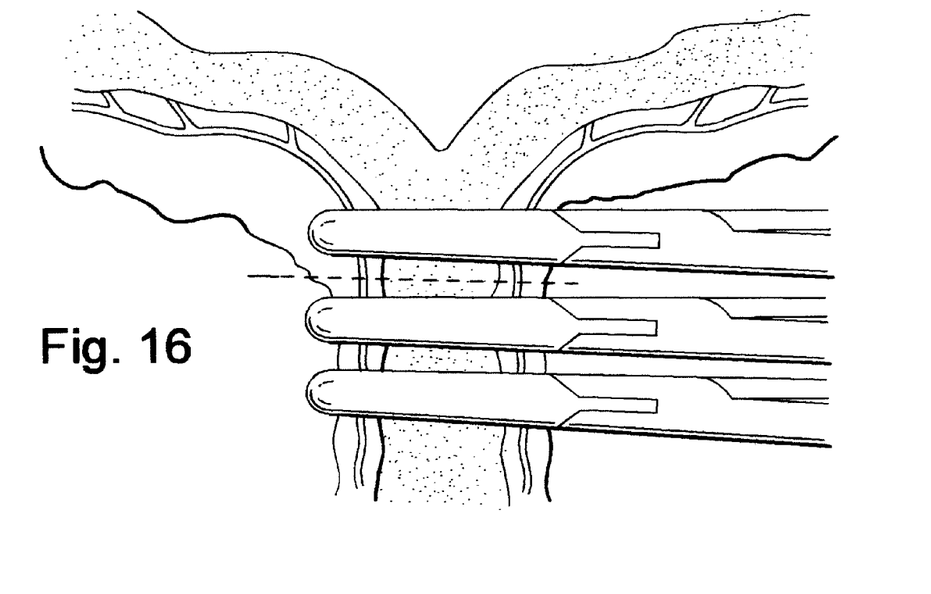
FIG. 16 is a plan view of the details of the uterine body which has been retracted to a position for surgical excision.
Figure 17:
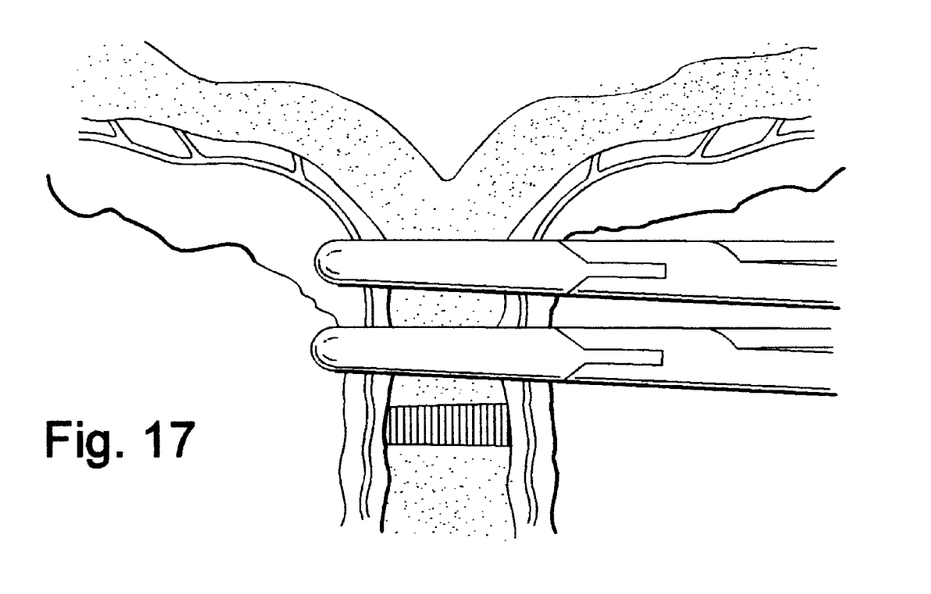
FIG. 17 is a continuation of the procedure shown in FIG. 17 wherein one clamp has been removed.
Figure 18:
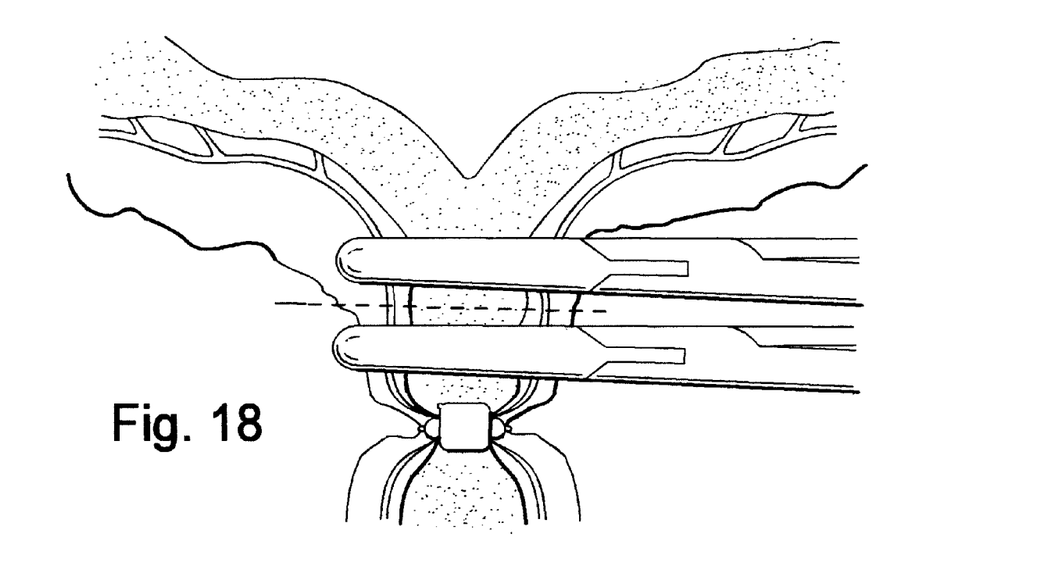
FIG. 18 is plan view similar to previous views where the incision location has been identified.
Figure 19:
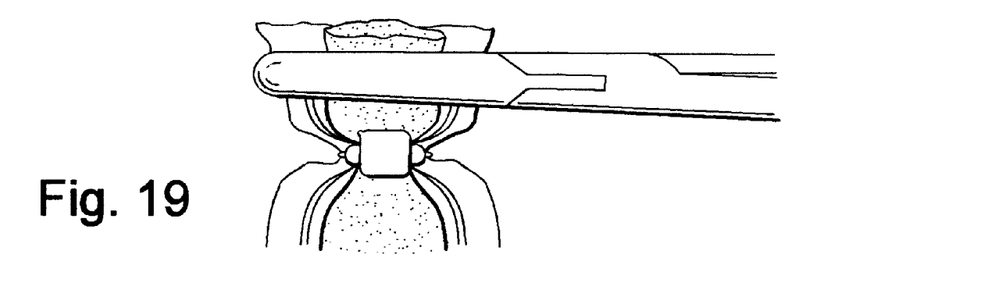
FIG. 19 is a plan view similar to those previously illustrated wherein the uterine stump is severed between the hemostats.
Figure 20:
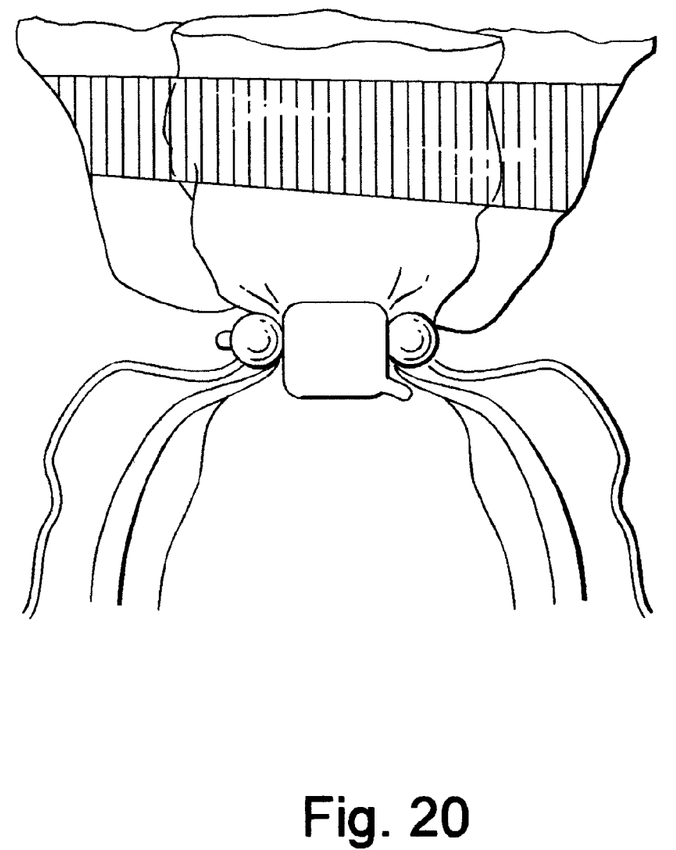
FIG. 20 is a plan view of the stump being inspected for hemostasis prior to being replaced into the abdomen.

FIG. 7 shows in sequence the movement of engaging elements 40 on first segment 32 through locking mechanism 36 and against teeth 44. A single tooth 44 will raise after being passed over by an engaging element 40 and the opposite offset tooth will partially open at that time. The sequence is reversed from row to row as engaging elements 40 engage the teeth one after the other.

Figure 5:
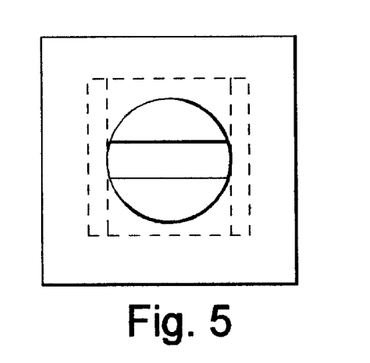
FIG. 5 is an end elevational and sectional view of the device shown in FIG. 3 taken along the line 5—5.
Figure 6:
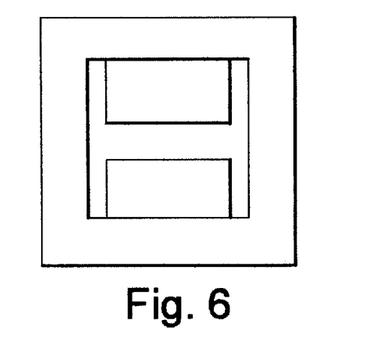
FIG. 6 is an end elevational and sectional vie of the device shown in FIG. 3 taken along the line 6—6.

FIGS. 5 and 6 show sectional views of locking mechanism 36 with FIG. 5 disclosing the exterior end elevational view showing a circular opening through which engaging elements 40 can pass. In FIG. 6, the sectional view is taken along line 6—6 showing the positioning of teeth 44 at that location.

In the method of the present invention, the cinch suture is used to close an opening created by, for example, the surgical excision of an organ or vessel to remove undesired parts such as ovaries or testicles. The method includes passing first segment 32 through locking mechanism 36 to form an endless loop, positioning the endless loop around the opening, and pulling first segment 32 through locking mechanism 36 to tighten the loop and close the opening while holding second segment 34 in a fixed position. To provide a neat closure, the unused portion of first and second segments 32, 34 are usually removed.

The method in detail, for example, wherein an opening formed by surgical excision of an organ or vessel includes the complete steps of opening the body to gain access to the organ or vessel in the holding cavity, retracting the organ or vessel to a position for surgical excision, clamping the organ or vessel to isolate the excision location, excising the organ or vessel at the isolated location while maintaining the clamps in position, passing first segment 32 through locking mechanism 36 to form an endless loop, positioning the endless loop around the opening, pulling first segment 32 through locking mechanism 36 to tighten the loop and closing the opening while holding second segment 34 in a fixed position. Thereafter, the unused portions of first and second segments 32, 34 are removed, the clamps are removed, and the closed opening organ or vessel is replaced in the original retaining cavity. Standard surgical procedures are used for closing the cavity.

Since the device of the present invention is preferably molded so that it can be form of a non-toxic and bacteria resistant material, it can be made in various sizes by creating different molds for each size desired. There are presently non-autoclavical materials available so that a cold anti-bacteria treatment can be utilized.

The present invention represents an extremely efficient and expedient way to positively close openings created by surgical excision. Once the created opening has been sealed, it can be examined for leakage and thereafter finalized by trimming the excess ends of the first and second segments. Once inspected and trimmed, the closed opening, if it is a result of surgical excision, can be replaced with the organ or vessel in the original retaining cavity and the cavity closed by normal surgical closure procedures.

Thus it can be seen that a cinch suture and method of using that suture have been provided that will meet all the advantages of prior art devices and offer additional advantages not heretofore achievable. With respect to the present invention, the optimum dimensional relationship to the parts of the invention including variations in size, materials, shape, form, function and manner of operation, use and assembly are deemed readily apparent to those skilled in the art, and all equivalent relationships illustrated in the drawings and used and described in the specification are intended to be encompassed herein.

The foregoing is considered as illustrative only of the principles of the invention. Numerous modifications and changes will readily occur to those skilled in the art, and it is not desired to limit the invention to the exact construction and operation shown and described. All suitable modifications and equivalents that fall within the scope of the appended claims are deemed to be within the present inventive concept.

What is claimed is:

1. A cinch suture for use with a surgical excision comprising: a first segment; a second segment; and a locking mechanism joining the first and second segments, the first segment having a plurality of engaging elements carried thereby and a locking mechanism having teeth positioned to interact with some of the engaging elements as the first segment is passed through the locking mechanism to secure the first segment against removal wherein the first segment has a working end and the second segment has a stationary end, the locking mechanism teeth are flexible and movable, and the teeth are arranged in two rows in a face-to-face offset relationship.

2. The cinch suture as claimed in claim 1 where the first segment engaging elements each have a spherical configuration.

3. The cinch suture as claimed in claim 1 wherein the first segment passing through the locking mechanism forms an endless loop for encircling and closing an opening formed by the surgical excision of an organ or vessel.

4. The cinch suture as claimed in claim 3 wherein the first segment engaging elements each have a spherical configuration.

5. The cinch suture as claimed in claim 2 wherein the locking mechanism has a segment receiving entrance and a segment removal exit and the first working end facilitates the positioning of the first segment into the segment receiving entrance and out of the segment removal exit.

6. The cinch suture as claimed in claim 1 wherein the engaging elements alternately engage the two rows of offset teeth as the engaging elements are moved between the offset teeth rows to provide incremental adjustment in the tightness of the suture and to place pressure on the suture to hold the suture firmly in place.

7. The cinch suture as claimed in claim 6 wherein the engaging elements each have a spherical configuration and are formed along an extended length of the first segment.

8. The cinch suture as claimed in claim 2 wherein the first segment passing through the locking mechanism forms an endless loop for encircling and closing an opening formed by the surgical excision of an organ or vessel, the locking mechanism has a segment receiving entrance and a segment removal exit and the first working end facilitates the positioning of the first segment into the segment receiving entrance and out of the segment removal exit and the spherical engaging elements alternately engage the two rows of offset teeth as the engaging elements are moved between the offset teeth rows to provide incremental adjustment in the tightness of the suture and place pressure on the suture to hold the suture firmly in place.

9. A method of applying a cinch suture having first and second segments and a locking mechanism around an opening to close the opening comprising the steps of: passing the first segment through the locking mechanism to form an endless loop; positioning the endless loop around the opening; pulling the first segment through the locking mechanism to tighten the loop and close the opening while holding the second segment in a fixed position; and removing the unused portions of the first and second segments.

10. A method of applying a cinch suture having first and second segments and a locking mechanism around an opening formed by the surgical incision of an organ or vessel comprising the steps of: opening the body to gain access to the organ or vessel and the holding cavity; retracting the organ or vessel into position for surgical excision; clamping the organ or vessel to isolate the incision location; incising the organ or vessel at the isolated location while maintaining the clamps in position; passing the first segment through the locking mechanism to form an endless loop; positioning the endless loop around the opening; pulling the first segment through the locking mechanism to tighten the loop and close the opening while holding the second segment in a fixed position; removing the unused portions of the first and second segments; removing the clamps; replacing the closed opening organ or vessel in the original retaining cavity; and closing the opened cavity.

* * * * *